(12) United States Patent
Brazzo

(10) Patent No.: US 11,253,545 B2
(45) Date of Patent: Feb. 22, 2022

(54) COMPOSITIONS COMPRISING SILVER NITRATE, HYALURONIC ACID AND ALLANTOIN AND METHODS FOR USE THEREOF

(71) Applicant: Brian Brazzo, New York, NY (US)

(72) Inventor: Brian Brazzo, New York, NY (US)

( * ) Notice: Subject to any disclaimer, the term of this patent is extended or adjusted under 35 U.S.C. 154(b) by 0 days.

(21) Appl. No.: 16/875,500

(22) Filed: May 15, 2020

(65) Prior Publication Data
US 2020/0368275 A1 Nov. 26, 2020

Related U.S. Application Data

(60) Provisional application No. 62/852,602, filed on May 24, 2019, provisional application No. 62/944,796, filed on Dec. 6, 2019.

(51) Int. Cl.
| | |
|---|---|
| *A61K 33/38* | (2006.01) |
| *A61K 31/4166* | (2006.01) |
| *A61K 31/728* | (2006.01) |
| *A61K 9/00* | (2006.01) |

(52) U.S. Cl.
CPC .......... *A61K 33/38* (2013.01); *A61K 31/4166* (2013.01); *A61K 31/728* (2013.01); *A61K 9/0014* (2013.01); *A61K 9/0048* (2013.01)

(58) Field of Classification Search
CPC .. A61K 33/38; A61K 31/4166; A61K 31/728; A61K 9/0014; A61K 9/0048; A61K 9/08
See application file for complete search history.

(56) References Cited

U.S. PATENT DOCUMENTS

2014/0213990 A1* 7/2014 Gorinshteyn .......... A61K 33/40 604/304
2015/0290173 A1* 10/2015 Divney .................. A61K 45/06 424/49

FOREIGN PATENT DOCUMENTS

| EP | 1 216 065 B1 | 9/2008 | |
|---|---|---|---|
| WO | WO-2006126212 A2 * | 11/2006 | ............. A61K 35/14 |
| WO | 2010/085123 A2 | 7/2010 | |

* cited by examiner

*Primary Examiner* — Quanglong N Truong
(74) *Attorney, Agent, or Firm* — Schneer IP Law PLLC

(57) ABSTRACT

In one embodiment, a composition is provided, comprising: 0.0005 wt % to 0.04 wt % of silver nitrate, based on a total weight of the composition; 0.01 wt % to 1.0 wt % of hyaluronic acid, based on the total weight of the composition; and 0.05 wt % to 2.5 wt % of allantoin, based on the total weight of the composition. In one embodiment, a method of treating a skin wound is provided, comprising: topically applying a sufficient amount of a composition to the skin wound of a patient to cover the skin wound, the composition comprising: 0.0005 wt % to 0.05 wt % of silver composition, based on a total weight of the composition; 0.01 wt % to 0.1 wt % of hyaluronic acid, based on the total weight of the composition; and 0.05 wt % to 2.5 wt % of allantoin, based on the total weight of the composition.

7 Claims, No Drawings

COMPOSITIONS COMPRISING SILVER NITRATE, HYALURONIC ACID AND ALLANTOIN AND METHODS FOR USE THEREOF

RELATED APPLICATIONS

This application claims priority to U.S. Provisional Application No. 62/852,602 filed May 24, 2019 and to U.S. Provisional Application No. 62/944,796 filed Dec. 6, 2019 each of which is incorporated herein by reference in its respective entirety for all purposes.

TECHNICAL FIELD

The present disclosure relates to healing compositions and methods of use thereof.

SUMMARY OF THE DISCLOSURE

In one embodiment, a composition is provided, comprising: 0.0005 wt % to 0.05 wt % of silver composition, based on a total weight of the composition; 0.01 wt % to 1.0 wt % of hyaluronic acid, based on the total weight of the composition; and 0.05 wt % to 2.5 wt % of allantoin, based on the total weight of the composition.

In one or more of the described embodiments, the silver composition comprises at least one of silver nitrate, colloidal silver, or any combination thereof.

In one or more of the described embodiments, the composition comprises 0.002 wt % to 0.007 wt % of the silver composition, based on the total weight of the composition.

In one or more of the described embodiments, the composition comprises 0.005 wt % of the silver composition, based on the total weight of the composition.

In one or more of the described embodiments, the composition comprises 0.1 wt % to 0.3 wt % of the hyaluronic acid, based on the total weight of the composition.

In one or more of the described embodiments, the composition comprises 0.2 wt % of the hyaluronic acid, based on the total weight of the composition.

In one or more of the described embodiments, the composition comprises 0.3 wt % to 1 wt % of the allantoin, based on the total weight of the composition.

In one or more of the described embodiments, the composition comprises 0.7 wt % of the allantoin, based on the total weight of the composition.

In one or more of the described embodiments, the composition comprises a humectant.

In one or more of the described embodiments, the humectant is a plant-based humectant.

In one or more of the described embodiments, the composition comprises 10 wt % to 30 wt % of the humectant, based on the total weight of the composition.

In one or more of the described embodiments, the composition comprises 22 wt % of the humectant, based on the total weight of the composition.

In one embodiment, a method of treating a skin wound is provided, comprising: topically applying a sufficient amount of a composition to the skin wound of a patient to cover the skin wound, the composition comprising: 0.0005 wt % to 0.05 wt % of silver composition, based on a total weight of the composition; 0.01 wt % to 0.1 wt % of hyaluronic acid, based on the total weight of the composition; and 0.05 wt % to 2.5 wt % of allantoin, based on the total weight of the composition.

In one or more of the described embodiments, the method comprises repeating the topically applying step 1 to 4 times per day over an initial 7 days and 1 to 2 times per day over a subsequent 30 days.

In one or more of the described embodiments, the method comprises repeating the topically applying step 2 to 4 times per day over 7 days.

In one or more of the described embodiments, the method comprises repeating the topically applying step 3 to 4 times per day over 7 days.

In one or more of the described embodiments, the method comprises repeating step the topically applying step 4 times per day over 7 days.

In one or more of the described embodiments, the method comprises a composition that comprises 0.002 wt % to 0.007 wt % of the silver composition, based on the total weight of the composition.

In one or more of the described embodiments, the method comprises a composition that comprises 0.1 wt % to 0.3 wt % of the hyaluronic acid, based on the total weight of the composition.

In one or more of the described embodiments, the method comprises a composition that comprises 0.3 wt % to 1 wt % of the allantoin, based on the total weight of the composition.

DETAILED DESCRIPTION

Embodiments of the present disclosure, briefly summarized above and discussed in greater detail below, can be understood by reference to the illustrative embodiments of the disclosure depicted in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. The figures are not drawn to scale and may be simplified for clarity. It is contemplated that elements and features of one embodiment may be beneficially incorporated in other embodiments without further recitation.

Among those benefits and improvements that have been disclosed, other objects and advantages of this disclosure can become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the disclosure may be readily combined, without departing from the scope or spirit of the disclosure. Further, when a particular feature, structure, or characteristic is described in connection with an implementation, it is submitted that it is within the knowledge of one skilled in the art to affect such feature, structure, or characteristic in connection with other implementations whether or not explicitly described herein.

The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, "silver composition" includes any silver-containing composition or compound. For example, in some non-limiting embodiments, a "silver composition" may include silver nitrate. In some non-limiting embodiments, a "silver composition" may include colloidal silver. In some embodiments, a "silver composition" may include a silver gel. In some non-limiting embodiments, a "silver composition" may include any combination of one or more exemplary silver compositions described herein.

In some embodiments, the present disclosure relates to a composition comprising silver composition, hyaluronic acid and allantoin for treatment of skin wounds. In embodiments, the composition comprises 0.001 wt % to 0.01 wt % of silver composition, based on a total weight of the composition; 0.05 wt % to 0.5 wt % of hyaluronic acid, based on the total weight of the composition; and 0.1 wt % to 2 wt % of allantoin, based on the total weight of the composition.

In embodiments, the composition includes 0.0005 wt % to 0.05 wt % of silver composition, based on a total weight of the composition. In embodiments, the composition includes 0.0005 wt % to 0.04 wt % of silver composition, based on a total weight of the composition. In embodiments, the composition includes 0.0005 wt % to 0.03 wt % of silver composition, based on a total weight of the composition. In embodiments, the composition includes 0.0005 wt % to 0.02 wt % of silver composition, based on a total weight of the composition. In embodiments, the composition includes 0.0005 wt % to 0.01 wt % of silver composition, based on a total weight of the composition. In embodiments, the composition includes 0.0005 wt % to 0.005 wt % of silver composition, based on a total weight of the composition. In embodiments, the composition includes 0.0005 wt % to 0.001 wt % of silver composition, based on a total weight of the composition.

In embodiments, the composition includes 0.001 wt % to 0.01 wt % of silver composition, based on a total weight of the composition. In embodiments, the composition includes 0.001 wt % to 0.009 wt % of silver composition, based on a total weight of the composition. In embodiments, the composition includes 0.001 wt % to 0.008 wt % of silver composition, based on a total weight of the composition. In embodiments, the composition includes 0.001 wt % to 0.007 wt % of silver composition, based on a total weight of the composition. In embodiments, the composition includes 0.001 wt % to 0.006 wt % of silver composition, based on a total weight of the composition. In embodiments, the composition includes 0.001 wt % to 0.005 wt % of silver composition, based on a total weight of the composition. In embodiments, the composition includes 0.001 wt % to 0.004 wt % of silver composition, based on a total weight of the composition. In embodiments, the composition includes 0.001 wt % to 0.003 wt % of silver composition, based on a total weight of the composition. In embodiments, the composition includes 0.001 wt % to 0.002 wt % of silver composition, based on a total weight of the composition.

In embodiments, the composition includes 0.001 wt % to 0.01 wt % of silver composition, based on a total weight of the composition. In embodiments, the composition includes 0.002 wt % to 0.01 wt % of silver composition, based on a total weight of the composition. In embodiments, the composition includes 0.003 wt % to 0.01 wt % of silver composition, based on a total weight of the composition. In embodiments, the composition includes 0.004 wt % to 0.01 wt % of silver composition, based on a total weight of the composition. In embodiments, the composition includes 0.005 wt % to 0.01 wt % of silver composition, based on a total weight of the composition. In embodiments, the composition includes 0.006 wt % to 0.01 wt % of silver composition, based on a total weight of the composition. In embodiments, the composition includes 0.007 wt % to 0.01 wt % of silver composition, based on a total weight of the composition. In embodiments, the composition includes 0.008 wt % to 0.01 wt % of silver composition, based on a total weight of the composition. In embodiments, the composition includes 0.009 wt % to 0.01 wt % of silver composition, based on a total weight of the composition.

In embodiments, the composition includes 0.001 wt % to 0.05 wt % of silver composition, based on a total weight of the composition. In embodiments, the composition includes 0.005 wt % to 0.05 wt % of silver composition, based on a total weight of the composition. In embodiments, the composition includes 0.01 wt % to 0.05 wt % of silver composition, based on a total weight of the composition. In embodiments, the composition includes 0.02 wt % to 0.05 wt % of silver composition, based on a total weight of the composition. In embodiments, the composition includes 0.03 wt % to 0.05 wt % of silver composition, based on a total weight of the composition. In embodiments, the composition includes 0.04 wt % to 0.05 wt % of silver composition, based on a total weight of the composition.

In embodiments, the composition includes 0.002 wt % to 0.009 wt % of silver composition, based on a total weight of the composition. In embodiments, the composition includes 0.003 wt % to 0.008 wt % of silver composition, based on a total weight of the composition. In embodiments, the composition includes 0.004 wt % to 0.007 wt % of silver composition, based on a total weight of the composition. In embodiments, the composition includes 0.005 wt % to 0.006 wt % of silver composition, based on a total weight of the composition.

In embodiments, the composition includes 0.0005 wt. %, 0.0006 wt. %, 0.0007 wt. %, 0.0008 wt. %, 0.0009 wt. %, 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.02 wt %, 0.03 wt %, 0.04 wt % or 0.05 wt % of silver composition, based on a total weight of the composition.

In embodiments, the composition includes 0.01 wt % to 1.0 wt % of hyaluronic acid, based on the total weight of the composition. In embodiments, the composition includes 0.01 wt % to 0.9 wt % of hyaluronic acid, based on the total weight of the composition. In embodiments, the composition includes 0.01 wt % to 0.8 wt % of hyaluronic acid, based on the total weight of the composition. In embodiments, the composition includes 0.01 wt % to 0.75 wt % of hyaluronic acid, based on the total weight of the composition. In embodiments, the composition includes 0.01 wt % to 0.5 wt % of hyaluronic acid, based on the total weight of the composition. In embodiments, the composition includes 0.01 wt % to 0.25 wt % of hyaluronic acid, based on the total weight of the composition. In embodiments, the composition includes 0.01 wt % to 0.1 wt % of hyaluronic acid, based on the total weight of the composition. In embodiments, the composition includes 0.01 wt % to 0.05 wt % of hyaluronic acid, based on the total weight of the composition. In embodiments, the composition includes 0.01 wt % to 0.04 wt % of hyaluronic acid, based on the total weight of the composition. In embodiments, the composition includes 0.01 wt % to 0.03 wt % of hyaluronic acid, based on the total weight of the composition. In embodiments, the composition includes 0.01 wt % to 0.02 wt % of hyaluronic acid, based on the total weight of the composition.

In embodiments, the composition includes 0.05 wt % to 0.7 wt % of hyaluronic acid, based on the total weight of the composition. In embodiments, the composition includes 0.05 wt % to 0.6 wt % of hyaluronic acid, based on the total weight of the composition. In embodiments, the composition includes 0.05 wt % to 0.5 wt % of hyaluronic acid, based on the total weight of the composition. In embodiments, the composition includes 0.05 wt % to 0.4 wt % of hyaluronic acid, based on the total weight of the composition. In embodiments, the composition includes 0.05 wt % to 0.3 wt % of hyaluronic acid, based on the total weight of the composition. In embodiments, the composition includes 0.05 wt % to 0.25 wt % of hyaluronic acid, based on the total weight of the composition. In embodiments, the composition includes 0.05 wt % to 0.2 wt % of hyaluronic acid, based on the total weight of the composition. In embodiments, the composition includes 0.05 wt % to 0.1 wt % of hyaluronic acid, based on the total weight of the composition.

In embodiments, the composition includes 0.1 wt % to 0.7 wt % of hyaluronic acid, based on the total weight of the composition. In embodiments, the composition includes 0.2 wt % to 0.7 wt % of hyaluronic acid, based on the total weight of the composition. In embodiments, the composition includes 0.25 wt % to 0.7 wt % of hyaluronic acid, based on the total weight of the composition. In embodiments, the composition includes 0.3 wt % to 0.7 wt % of hyaluronic acid, based on the total weight of the composition. In embodiments, the composition includes 0.4 wt % to 0.7 wt % of hyaluronic acid, based on the total weight of the composition. In embodiments, the composition includes 0.5 wt % to 0.7 wt % of hyaluronic acid, based on the total weight of the composition. In embodiments, the composition includes 0.6 wt % to 0.7 wt % of hyaluronic acid, based on the total weight of the composition. In embodiments, the composition includes 0.05 wt % to 0.7 wt % of hyaluronic acid, based on the total weight of the composition.

In embodiments, the composition includes 0.1 wt % to 0.6 wt % of hyaluronic acid, based on the total weight of the composition. In embodiments, the composition includes 0.2 wt % to 0.5 wt % of hyaluronic acid, based on the total weight of the composition. In embodiments, the composition includes 0.3 wt % to 0.4 wt % of hyaluronic acid, based on the total weight of the composition. In embodiments, the composition includes 0.25 wt % to 0.3 wt % of hyaluronic acid, based on the total weight of the composition.

In embodiments, the composition includes 0.02 wt % to 1.0 wt % of hyaluronic acid, based on the total weight of the composition. In embodiments, the composition includes 0.03 wt % to 1.0 wt % of hyaluronic acid, based on the total weight of the composition. In embodiments, the composition includes 0.04 wt % to 1.0 wt % of hyaluronic acid, based on the total weight of the composition. In embodiments, the composition includes 0.05 wt % to 1.0 wt % of hyaluronic acid, based on the total weight of the composition. In embodiments, the composition includes 0.1 wt % to 1.0 wt % of hyaluronic acid, based on the total weight of the composition. In embodiments, the composition includes 0.25 wt % to 1.0 wt % of hyaluronic acid, based on the total weight of the composition. In embodiments, the composition includes 0.5 wt % to 1.0 wt % of hyaluronic acid, based on the total weight of the composition. In embodiments, the composition includes 0.75 wt % to 1.0 wt % of hyaluronic acid, based on the total weight of the composition. In embodiments, the composition includes 0.8 wt % to 1.0 wt % of hyaluronic acid, based on the total weight of the composition. In embodiments, the composition includes 0.9 wt % to 1.0 wt % of hyaluronic acid, based on the total weight of the composition.

In embodiments, the composition includes 0.01 wt %, 0.02 wt %, 0.03 wt %, 0.04 wt %, 0.05 wt %, 0.06 wt %, 0.07 wt %, 0.08 wt %, 0.09 wt %, 0.1 wt %, 0.15 wt %, 0.1 wt %, 0.25 wt %, 0.3 wt %, 0.35 wt %, 0.4 wt %, 0.45 wt %, 0.5 wt %, 0.55 wt %, 0.6 wt %, 0.65 wt %, 0.7 wt %, 0.75 wt %, 0.8 wt %, 0.85 wt %, 0.9 wt %, 0.95 wt %, or 1.0 wt % of hyaluronic acid, based on the total weight of the composition.

In some embodiments, the hyaluronic acid is present in the composition as a salt. In some embodiments, the hyaluronic acid is present in the composition as a salt of sodium (i.e., as sodium hyaluronate) or potassium (i.e., as potassium hyaluronate).

In some embodiments, the composition includes 0.05 wt % to 2.5 wt % of allantoin, based on a total weight of the composition. In embodiments, the composition includes 0.05 wt % to 2.0 wt % of allantoin, based on a total weight of the composition. In embodiments, the composition includes 0.05 wt % to 1.5 wt % of allantoin, based on a total weight of the composition. In embodiments, the composition includes 0.05 wt % to 1.0 wt % of allantoin, based on a total weight of the composition. In embodiments, the composition includes 0.05 wt % to 0.5 wt % of allantoin, based on a total weight of the composition. In embodiments, the composition includes 0.05 wt % to 0.25 wt % of allantoin, based on a total weight of the composition. In embodiments, the composition includes 0.05 wt % to 0.1 wt % of allantoin, based on a total weight of the composition.

In embodiments, the composition includes 0.1 wt % to 2.5 wt % of allantoin, based on a total weight of the composition. In embodiments, the composition includes 0.25 wt % to 2.5 wt % of allantoin, based on a total weight of the composition. In embodiments, the composition includes 0.5 wt % to 2.5 wt % of allantoin, based on a total weight of the composition. In embodiments, the composition includes 1.0 wt % to 2.5 wt % of allantoin, based on a total weight of the composition. In embodiments, the composition includes 2.0 wt % to 2.5 wt % of allantoin, based on a total weight of the composition.

In embodiments, the composition includes 0.1 wt % to 2.0 wt % of allantoin, based on a total weight of the composition. In embodiments, the composition includes 0.25 wt % to 1.5 wt % of allantoin, based on a total weight of the composition. In embodiments, the composition includes 0.5 wt % to 1.0 wt % of allantoin, based on a total weight of the composition.

In embodiments, the composition includes 0.1 wt % to 1.8 wt % of allantoin, based on a total weight of the composition. In embodiments, the composition includes 0.1 wt % to 1.6 wt % of allantoin, based on a total weight of the composition. In embodiments, the composition includes 0.1 wt % to 1.4 wt % of allantoin, based on a total weight of the composition. In embodiments, the composition includes 0.1 wt % to 1.3 wt % of allantoin, based on a total weight of the composition. In embodiments, the composition includes 0.1 wt % to 1.2 wt % of allantoin, based on a total weight of the composition. In embodiments, the composition includes 0.1 wt % to 1.1 wt % of allantoin, based on a total weight of the composition. In embodiments, the composition includes 0.1 wt % to 1 wt % of allantoin, based on a total weight of the composition. In embodiments, the composition includes 0.1 wt % to 0.9 wt % of allantoin, based on a total weight of the composition. In embodiments, the composition includes 0.1 wt % to 0.8 wt % of allantoin, based on a total weight of the composition. In embodiments, the composition includes 0.1 wt % to 0.7 wt % of allantoin, based on a total weight of the composition. In embodiments, the composition includes 0.1 wt % to 0.6 wt % of allantoin, based on a total weight of the composition. In embodiments, the composition includes 0.1 wt % to 0.5 wt % of allantoin, based on a total weight of the composition. In embodiments, the composition includes 0.1 wt % to 0.4 wt % of allantoin, based on a total weight of the composition. In embodiments, the composition includes 0.1 wt % to 0.3 wt % of allantoin, based on a total weight of the composition. In embodiments, the composition includes 0.1 wt % to 0.2 wt % of allantoin, based on a total weight of the composition.

In embodiments, the composition includes 0.2 wt % to 2 wt % of allantoin, based on a total weight of the composition. In embodiments, the composition includes 0.3 wt % to 2 wt % of allantoin, based on a total weight of the composition. In embodiments, the composition includes 0.4 wt % to 2 wt % of allantoin, based on a total weight of the composition. In embodiments, the composition includes 0.5 wt % to 2 wt % of allantoin, based on a total weight of the composition. In embodiments, the composition includes 0.6 wt % to 2 wt % of allantoin, based on a total weight of the composition. In embodiments, the composition includes 0.7 wt % to 2 wt % of allantoin, based on a total weight of the composition. In embodiments, the composition includes 0.8 wt % to 2 wt % of allantoin, based on a total weight of the composition. In embodiments, the composition includes 0.9 wt % to 2 wt % of allantoin, based on a total weight of the composition. In embodiments, the composition includes 1 wt % to 2 wt % of allantoin, based on a total weight of the composition. In embodiments, the composition includes 1.1 wt % to 2 wt % of allantoin, based on a total weight of the composition. In embodiments, the composition includes 1.2 wt % to 2 wt % of allantoin, based on a total weight of the composition. In embodiments, the composition includes 1.3 wt % to 2 wt % of allantoin, based on a total weight of the composition. In embodiments, the composition includes 1.4 wt % to 2 wt % of allantoin, based on a total weight of the composition. In embodiments, the composition includes 1.6 wt % to 2 wt % of allantoin, based on a total weight of the composition. In embodiments, the composition includes 1.8 wt % to 2 wt % of allantoin, based on a total weight of the composition.

In embodiments, the composition includes 0.2 wt % to 1.8 wt % of allantoin, based on a total weight of the composition. In embodiments, the composition includes 0.3 wt % to 1.6 wt % of allantoin, based on a total weight of the composition. In embodiments, the composition includes 0.4 wt % to 1.4 wt % of allantoin, based on a total weight of the composition. In embodiments, the composition includes 0.5 wt % to 1.2 wt % of allantoin, based on a total weight of the composition. In embodiments, the composition includes 0.6 wt % to 1 wt % of allantoin, based on a total weight of the composition. In embodiments, the composition includes 0.7 wt % to 0.9 wt % of allantoin, based on a total weight of the composition.

In embodiments, the composition includes 0.05 wt %, 0.06 wt %, 0.07 wt %, 0.08 wt %, 0.09 wt %, 0.1 wt %, 0.2 wt %, 0.3 wt %, 0.4 wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1%, 2.2%, 2.3%, 2.4%, or 2.5% of allantoin, based on a total weight of the composition.

In some non-limiting embodiments, the composition consists essentially of the silver composition, hyaluronic acid, and allantoin. In some embodiments, the composition consists essentially of the silver composition, hyaluronic acid, and allantoin in the any amount or combination of amounts described herein. In some embodiments, "consisting essentially of" allows for addition of components other than the silver composition, hyaluronic acid, and allantoin, so long as the added components do not materially affect the wound healing properties described herein. In some embodiments, permissible added components may include, but are not limited to any additional component(s) in any amount(s) described herein, infra.

In some embodiments, the composition further includes a humectant.

In embodiments, the humectant includes, but is not limited to diols (e.g., 1,3 propanediol, propylene glycol), or glycerol.

In some embodiments, the humectant is a plant or fungus-based humectant. In some embodiments, the plant or fungus based humectant is silver ear mushroom extract.

In embodiments, the composition includes 10 wt % to 30 wt % of the humectant, based on the total weight of the composition. In embodiments, the composition includes 10 wt % to 25 wt % of the humectant, based on the total weight of the composition. In embodiments, the composition includes 10 wt % to 20 wt % of the humectant, based on the total weight of the composition. In embodiments, the composition includes 10 wt % to 15 wt % of the humectant, based on the total weight of the composition. In embodiments, the composition includes 15 wt % to 30 wt % of the humectant, based on the total weight of the composition. In embodiments, the composition includes 20 wt % to 30 wt % of the humectant, based on the total weight of the composition. In embodiments, the composition includes 25 wt % to 30 wt % of the humectant, based on the total weight of the composition. In embodiments, the composition includes 15 wt % to 25 wt % of the humectant, based on the total weight of the composition.

In embodiments, the composition includes 10 wt %, 15 wt %, 20 wt %, 22 wt %, 25 wt %, or 30 wt % of the humectant, based on the total weight of the composition.

In one or more embodiment detailed herein, the composition further includes a base. In embodiments, the base includes, but is not limited to, a fatty acid, a silicone compound, water, a water-soluble plant extract (e.g., aloe juice, coconut water, orange water), or combinations thereof. In some embodiments, the water is purified water. In some embodiments, the purified water is distilled water. In some embodiments, the base may be present in from 10 to 95 wt %, based on the total weight of the composition.

In one or more embodiment detailed herein, the composition further includes at least one rheology modifier. In some embodiments the at least one rheology modifier includes one or more thickeners. In embodiments, the thickeners include, but are not limited to, ethylene glycol, propylene glycol, 1,3-propanediol, glycerol, sorbitol, xanthan gum, phenoxyethanol, maltodextrin, or combinations thereof. In some embodiments, the thickeners may be present from 0.1 to 50 wt % of the composition.

In one or more embodiment detailed herein, the composition further includes a gelling agent. In some embodiments, the gelling agent includes, but is not limited to, carbomer, cetyl alcohol, stearyl alcohol, carnauba wax, and stearic acid locust bean gum, xanthan gum, gelatin silica, bentonite, magnesium aluminum silicate, or combinations thereof. In some embodiments, the gelling agent may be present from 0.1 to 50 wt % of the composition.

In one or more embodiment detailed herein, the composition further includes a preservative. In some embodiments, the preservative includes, but is not limited to, methylparaben, propylparaben, butylparaben, ethylparaben, potassium sorbate, trisodium EDTA, phenoxyethanol, caprylyl glycol, ethyl alcohol, benzyl alcohol, diazolidinyl urea, imidazolidinyl urea, quaternium-15, or combinations thereof. In some embodiments, the preservative may be present from 0.1 to 50 wt % of the composition.

In one or more embodiment detailed herein, the composition further includes an amino acid. In some embodiments, the amino acid includes, but is not limited to, alanine, arginine, arginine hcl, asparagine, aspartic acid, calcium glycinate, cysteine, cysteine hcl, cystine, glutamic acid, glutamine, glycine, histidine, histidine hcl, isoleucine, leucine, lysine, lysine hcl, magnesium aspartate, methionine, phenylalanine, potassium aspartate, proline, serine, sodium glutamate, sodium glycinate, threonine, tryptophan, tyrosine, or combinations thereof. In some embodiments, the amino acid may be present from 0.1 to 50 wt % of the composition.

In one or more embodiment detailed herein, the composition further includes an emulsifier. In some embodiments, the emulsifier includes, but is not limited to, glyceryl stearate, glyceryl palmitate, glyceryl arachidate, triethanolamine, 3-cyclohexene-1-methanol, alpha, 4-dimethyl-alpha-(4-methyl-3-pentenyl) or combinations thereof. In some embodiments, the emulsifier may be present from 0.1 to 50 wt % of the composition.

In one or more embodiment detailed herein, the composition further includes a chelating agent. In some embodiments, the chelating agent includes, but is not limited to, EDTA, sodium phytate, sodium citrate, sodium gluconate, N-N-diacetic acid (and) tetra sodium salt or combinations thereof. In some embodiments, the chelating agent may be present from 0.1 to 50 wt % of the composition.

In one or more embodiment detailed herein, the composition includes other components such as diluents. The diluents act as a dispersant or carrier for other materials present in the composition, to facilitate their distribution when the composition is applied to the skin. Diluents other than water can include liquid or solid emollients, solvents, humectants, thickeners and/or powders.

In some embodiments, the composition may further include one or more anti-microbial agents. Non-limiting examples of anti-microbial agents include diglycerin, polyglyceryl-2-laurate, one or more glycols, or any combination thereof.

The composition may further comprise additional non-limiting cosmetic and/or pharmaceutical ingredients commonly used in the skin care industry, including, but not limited to, antioxidants, binders, biological additives, buffering agents, colorants, thickeners, polymers, astringents, fragrance, opacifying agents, conditioners, exfoliating agents, pH adjusters, preservatives, natural extracts, essential oils, skin sensates, skin soothing agents, and skin healing agents.

In embodiments, the composition is made using known methods in the art such as mixing the ingredients until homogenous.

In additional embodiments, an aspect of the present disclosure relates to a method of treating a skin wound that includes topically applying the composition of any embodiment detailed herein to the skin wound of a patient to treat the wound. In embodiments, a sufficient quantity of the composition is topically applied to cover the wound. In embodiments, a sufficient amount of the composition to cover the wound is applied 1 to 4 times per day for the first seven days. In embodiments, a sufficient amount of the composition to cover the wound is applied 1 to 3 times per day for the first seven days. In embodiments, a sufficient amount of the composition to cover the wound is applied 1 to 2 times per day for the first seven days. In embodiments, a sufficient amount of the composition to cover the wound is applied 2 to 4 times per day for the first seven days. In embodiments, a sufficient amount of the composition to cover the wound is applied 3 to 4 times per day for the first seven days. In embodiments, a sufficient amount of the composition to cover the wound is applied 1, 2, 3, or 4 times per day for the first seven days.

In embodiments, after the first seven days, a sufficient amount of the composition to cover the wound is applied 1 to 2 times per day for an additional month. In embodiments, after the first seven days, a sufficient amount of the composition to cover the wound is applied 1 or 2 times per day for an additional month.

In embodiments, the sufficient amount of the composition to cover the wound is 50 microliters to 350 microliters. In embodiments, the sufficient amount of the composition to cover the wound is 75 microliters to 250 microliters. In embodiments, the sufficient amount of the composition to cover the wound is 100 microliters to 250 microliters. In embodiments, the sufficient amount of the composition to cover the wound is 130 microliters to 250 microliters. In embodiments, the sufficient amount of the composition to cover the wound is 150 microliters to 250 microliters. In embodiments, the sufficient amount of the composition to cover the wound is 200 microliters to 250 microliters. In embodiments, the sufficient amount of the composition to cover the wound is 225 microliters to 250 microliters.

In embodiments, the sufficient amount of the composition to cover the wound is 50 microliters to 225 microliters. In embodiments, the sufficient amount of the composition to cover the wound is 50 microliters to 200 microliters. In embodiments, the sufficient amount of the composition to cover the wound is 50 microliters to 150 microliters. In embodiments, the sufficient amount of the composition to cover the wound is 50 microliters to 130 microliters. In embodiments, the sufficient amount of the composition to cover the wound is 50 microliters to 100 microliters. In embodiments, the sufficient amount of the composition to cover the wound is 50 microliters to 75 microliters.

In embodiments, the sufficient amount of the composition to cover the wound is 75 microliters to 225 microliters. In embodiments, the sufficient amount of the composition to cover the wound is 100 microliters to 200 microliters. In embodiments, the sufficient amount of the composition to cover the wound is 130 microliters to 150 microliters.

In embodiments, the wound requiring treatment is located in the skin around the eye. In embodiments, the wound requiring treatment includes one or more sutures. In embodiments, the wound requiring treatment is on the eyelid of a mammal, such as but not limited to the eyelid of a human. In embodiments, the wound is from surgery on or around the eyelid.

NON-LIMITING EXAMPLES

Non-limiting examples of the present disclosure are detailed below. A composition according to embodiments of the present disclosure comprising: (i) 0.005 wt % silver nitrate, (ii) 0.7 wt % allantoin, (iii) 0.23 wt % hyaluronic acid, (iv) 22 wt % plant-based humectants and (v) the remainder distilled water, glycerol, 1,3-propanediol, a preservative as detailed herein, an amino acid as detailed herein, an emulsifier as detailed herein, a gelling agent as detailed herein, and a chelating agent as detailed herein was formed by mixing the ingredients until the mixture was homogenous. Comparative compositions comprising: (i) two or less of 0.005 wt % silver nitrate, 0.7 wt % allantoin, and 0.23 wt % hyaluronic acid, (ii) 22 wt % plant-based humectants and (iii) the remainder distilled water, glycerol, 1,3-propanediol, a preservative as detailed herein, an amino acid as detailed herein, an emulsifier as detailed herein, a gelling agent as detailed herein, and a chelating agent as detailed herein were also formed by mixing the ingredients until the mixture was homogenous. The known topical antibiotic Neosporin® was also used as comparative composition. A sufficient amount of the composition or comparative composition was applied to 29 patients to cover substantially similar eyelid wounds with sutures. The compositions were applied 2 times daily for a week and 1 time daily for the next month. After the relevant time period, the wound was visually inspected and given a grade of healing based on the following 1-4 scale:

Wound healing scale, 1 week

1—wound with 1-3 mm lumps; sutures not dissolved; scar is visible to observer when eyes closed; significant crusting of dried blood on suture line.

2—wound with 1 mm lumps, sutures partially dissolved; scar partially visible to observer when eyes closed; mild crusting of dried blood on sutures.

3—wound with few small lumps; sutures mostly dissolved; scar barely noticeable to observer; minimal crusting on wound.

4—soft smooth wound; sutures dissolved; scar not noticeable to observer; no crusting.

Wound healing scale, 1 month

1—wound with 1-3 mm lumps; sutures partially dissolved with suture tracks in skin; scar is visible when eyes closed; persistent crusting of blood or debris on suture line.

2—would with 1 mm lumps; some suture remnants persist on wound; scar partially visible to observer when eyes closed; mild crusting of debris on suture line.

3—wound mostly smooth; sutures dissolved; scar barely noticeable; minimal wound crusting.

4—soft smooth wound; sutures completely dissolved; scar not noticeable; no crusting.

The results are shown in Table 1 below:

TABLE 1

| Patient No. | Composition/ Comparative Composition | Silver Composition | Hyaluronic acid | Allantoin | Neosporin ® | Time Period | Description | Grade |
| --- | --- | --- | --- | --- | --- | --- | --- | --- |
| 1 | Composition | Yes | Yes | Yes | No | 1 week | Soft flat, smooth; sutures dissolved; incision line not visible | 4 |
| 2 | Composition | Yes | Yes | Yes | No | 1 week | wound is almost invisible, sutures dissolved, wound soft, flat, smooth | 4 |
| 3 | Comparative Composition | No | No | No | No | 1 month | Wound with 1 mm lumps, elevated visible thick scar; mild crusting on wound | 2 |
| 4 | Composition | Yes | Yes | Yes | No | 1 week | Few small lumps; sutures mostly dissolved; minimal crusting; scar barely noticeable | 3 |
| 5 | Comparative Composition | Yes | No | No | No | 1 week | Moderate lumps and significant crusting. Sutures poorly dissolved. | 1 to 2 (1.5) |
| 6 | Comparative Composition | Yes | No | No | No | 1 week | Small lumps; Sutures mostly dissolved; minimal crusting | 3 |
| 7 | Comparative Composition | Yes | No | No | No | 1 week | Wound with few lumps; sutures mostly dissolved with minimal crusting | 3 |
| 8 | Comparative Composition | No | No | No | Yes | 1 month | Multiple bumps >3 mm, large crusts, sutures not dissolved | 1 |
| 9 | Composition | Yes | Yes | Yes | No | 4 days | wound is almost invisible, sutures dissolved, wound soft, flat, smooth | 3-4 (3.5) |
| 10 | Composition | Yes | Yes | Yes | No | 4 days | wound is almost invisible, sutures dissolved, wound soft, flat, smooth | 4 |

TABLE 1-continued

| Patient No. | Composition/ Comparative Composition | Silver Composition | Hyaluronic acid | Allantoin | Neosporin ® | Time Period | Description | Grade |
|---|---|---|---|---|---|---|---|---|
| 11 | Composition | Yes | Yes | Yes | No | 2 weeks | wound is almost invisible, sutures dissolved, wound soft, flat, smooth | 4 |
| 12 | Composition | Yes | Yes | Yes | No | 2 weeks | wound is almost invisible, sutures dissolved, wound soft, flat, smooth | 4 |
| 13 | Comparative Composition | Yes | No | No | No | 2 weeks | Average healing, some lumpiness. | 3 |
| 14 | Composition | Yes | Yes | Yes | No | 1 month | Soft flat, normal crease scar, hard to tell patient had surgery. | 4 |
| 15 | Comparative Composition | Yes | No | No | No | 1 Month | Some medial lumpiness right above left upper lid; minimal crusting with sutures mostly dissolved | 3 |
| 16 | Composition | Yes | Yes | Yes | No | 3 days | Excellent healing, small crusting, minimal bruising, soft flat | 4 |
| 17 | Composition | Yes | Yes | Yes | No | 1 month | Patient has dark skin which often pigments heavier on suture line but usually resolves. Patient has mild pigmenting but soft flat; sutures dissolved, scar not noticeable | 4 |
| 18 | Comparative Composition | No | No | No | No | 1 month | More swelling inflammation, large lumps; lot of broken dried suture remnants and crusting. | 1-2 (1.5) |
| 19 | Comparative Composition | Yes | Yes | No | No | 1 month | Left lower lid lesion removed, large crust formed, and healing was slow over the month; visible scar with lumps | 1 |
| 20 | Comparative Composition | Yes | No | Yes | No | 2 weeks | Right lower lid lesion removed, slower healing than expected with moderate lumps and crusting; sutures poorly dissolved. | 2 |
| 21 | Comparative Composition | Yes | No | No | No | 1 Week | Lot of crusting and wrinkling of skin; sutures poorly dissolved | 2 |
|  | Comparative Composition |  |  |  |  | 1 month | Less crusting and dryness; sutures mostly dissolved; wound has few small lumps; barely noticeable scar | 3 |
| 22 | Comparative Composition | Yes | No | No | No | 1 Week | Lot of crusting and large scab for this small lesion; sutures poorly dissolved | 2 |
|  | Comparative Composition |  |  |  |  | 1 Month | Patient was much better but still redder than expected; sutures partially dissolved with mild crusting | 2 |

TABLE 1-continued

| Patient No. | Composition/ Comparative Composition | Silver Composition | Hyaluronic acid | Allantoin | Neosporin ® | Time Period | Description | Grade |
|---|---|---|---|---|---|---|---|---|
| 23 | Comparative Composition | Yes | No | Yes | No | 1 Week | Substantial dryness, crusting and lumpiness. | 2 |
| 24 | Comparative Composition | Yes | Yes | No | No | 1 Week | Substantial swelling but wound is mostly flat, few small lumps, sutures mostly dissolved with minimally noticeable scar; minimal crusting | 3 |
| 25 | Comparative Composition | Yes | Yes | No | No | 1 Week | Substantial lumpiness and soreness at outside corners of wound. | 2 |
| 26 | Comparative Composition | Yes | No | Yes | No | 1 Week | Significant lumpiness and crusting with poorly dissolved sutures | 2 |
| 27 | Comparative Composition | Yes | No | Yes | No | 1 Week | Several 1 mm lumps; sutures partially dissolved; scar is noticeable; mild crusting | 2 |
|  | Comparative Composition |  |  |  |  | 1 Month | lumpy at outside corner of wound with sutures mostly dissolved; mild crusting. | 3 |
| 28 | Comparative Composition | Yes | Yes | No | No | 1 Week | Outside portion of wound lumpy with mild crusting; sutures partially dissolved | 2 |
|  | Comparative Composition |  |  |  |  | 1 Month | Wound mostly smooth; sutures dissolved; scar not visible; mild crusting of wound | 3 |
| 29 | Comparative Composition | Yes | No | No | No | 1 Week | Substantial crusting and lumpiness, sore on outside corner of wound; scar is visible | 2 |

As detailed in the table above, the wound healing of Patient Nos. 1, 2, 4, 9-12, 14, 16 and 17 associated with the compositions according to embodiments of the present disclosure exceeded the wound healing associated with the comparative compositions. Moreover, the wound healing associated with the compositions according to embodiments of the present disclosure (Patient Nos. 1, 2, 4, 9-12, 14, 16 and 17) substantially exceeded the wound healing associated with compositions having the silver composition, hyaluronic acid, or allantoin, but not all three components (Patient Nos. 13, 15, and 19-29) suggesting a synergistic effect of the silver composition, hyaluronic acid, and allantoin in the compositions according to embodiments of the present disclosure.

While a number of embodiments of the present disclosure have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

The invention claimed is:

1. A method of treating a skin wound comprising:
topically applying a sufficient amount of a composition to the skin wound of a patient, so as to cover the skin wound, the composition comprising:
0.0005 wt % to 0.04 wt % of silver nitrate, based on a total weight of the composition;
0.01 wt % to 1 wt % of hyaluronic acid, based on the total weight of the composition; and
0.05 wt % to 2.5 wt % of allantoin, based on the total weight of the composition; and
repeating the topically applying step from 1 to 4 times per day over an initial 7 days and 1 to 2 times per day over a subsequent 30 days.

2. The method of claim 1, wherein the method comprises repeating the topically applying step from 2 to 4 times per day over 7 days.

3. The method of claim 1, wherein the method comprises repeating the topically applying step from 3 to 4 times per day over 7 days.

4. The method of claim 1, wherein the method comprises repeating the topically applying step 4 times per day over 7 days.

5. The method of claim 1, wherein the sufficient amount of the composition applied during the topically applying step is from 50 microliters to 350 microliters.

6. The method of claim 1, wherein the skin wound of the patient is present on an eyelid of the patient.

7. The method of claim 1, wherein the composition consists essentially of:
- 0.0005 wt % to 0.04 wt % of the silver nitrate, the based on a total weight of the composition;
- 0.01 wt % to 1.0 wt % of the hyaluronic acid, based on the total weight of the composition; and
- 0.05 wt % to 2.5 wt % of the allantoin, based on the total weight of the composition.

* * * * *